US006626831B2

United States Patent
Holley et al.

(10) Patent No.: US 6,626,831 B2
(45) Date of Patent: Sep. 30, 2003

(54) GATED ULTRASOUND IMAGING APPARATUS AND METHOD

(75) Inventors: Gregory L. Holley, Mountian View, CA (US); Richard M. Bennett, Half Moon Bay, CA (US); Edward A. Gardner, San Jose, CA (US); Samuel H. Maslak, Woodside, CA (US)

(73) Assignee: Acuson Corporation, Mountain View, CA (US)

( * ) Notice: Subject to any disclaimer, the term of this patent is extended or adjusted under 35 U.S.C. 154(b) by 53 days.

(21) Appl. No.: 09/767,189

(22) Filed: Jan. 22, 2001

(65) Prior Publication Data

US 2001/0005776 A1 Jun. 28, 2001

Related U.S. Application Data

(60) Division of application No. 09/378,236, filed on Aug. 19, 1999, which is a continuation of application No. 08/838,919, filed on Apr. 11, 1997, now Pat. No. 6,110,120, and a continuation of application No. 09/159,527, filed on Sep. 23, 1998, now Pat. No. 5,957,845.

(51) Int. Cl.[7] .................................................. A61B 8/00
(52) U.S. Cl. ....................................... 600/437; 600/443
(58) Field of Search ................................. 600/447, 443, 600/437, 454, 455, 450, 449

(56) References Cited

U.S. PATENT DOCUMENTS

| 4,712,037 A | 12/1987 | Verbeek et al. |
| 5,040,537 A | 8/1991 | Katakura |
| 5,111,823 A | 5/1992 | Cohen |
| 5,115,809 A | 5/1992 | Saitoh et al. |
| 5,190,766 A | 3/1993 | Ishihara |
| 5,195,520 A | 3/1993 | Schlief et al. |
| 5,215,680 A | 6/1993 | D'Arrigo |
| 5,219,401 A | 6/1993 | Cathignol et al. |
| 5,255,683 A | 10/1993 | Monaghan |
| 5,287,753 A | 2/1994 | Routh et al. |
| 5,313,948 A | 5/1994 | Murashita et al. |
| 5,331,964 A | 7/1994 | Trahey et al. |
| 5,358,466 A | 10/1994 | Aida et al. |
| 5,380,411 A | 1/1995 | Schlief |
| 5,396,285 A | 3/1995 | Hedberg et al. |
| 5,410,205 A | 4/1995 | Gururaja |
| 5,410,516 A | 4/1995 | Uhlendorf et al. |
| 5,417,213 A | 5/1995 | Prince |

(List continued on next page.)

FOREIGN PATENT DOCUMENTS

| EP | 0 357 164 | 4/1995 |
| EP | 0 770 352 A1 | 5/1997 |
| EP | 0123456 A2 | 1/2000 |
| GB | 2316 174 A | 2/1998 |

OTHER PUBLICATIONS

"HP Ultrasound Technologies—Viability." About HP Ultrasound Imaging, WWW document 1997.
"Small Spheres Lend to Big Ideas." Research News, Science vol. 267, Jan. 20, 1995.

(List continued on next page.)

*Primary Examiner*—Francis J. Jaworski
*Assistant Examiner*—Maulin Patel

(57) ABSTRACT

An ultrasound imaging system is programmed to acquire first ultrasonic image frames intermittently. These first frames, typically triggered frames synchronized with a selected portion of an ECG cycle, are optimized for high image quality of a contrast agent included in the tissue. The imaging system automatically acquires second ultrasonic image frames between at least some of the first frames. The second image frames are typically locator frames which are optimized for reduced degradation of the contrast agent. More of the second frames are acquired per unit time than first frames, and both the first and second frames are displayed, either superimposed over one another or in side-by-side relationship. In this way the user is provided with substantially continuous transducer locating information, yet contrast agent destruction between acquisitions of the first, triggered frames is reduced or eliminated.

9 Claims, 8 Drawing Sheets

U.S. PATENT DOCUMENTS

| | | |
|---|---|---|
| 5,417,214 A | 5/1995 | Roberts et al. |
| 5,425,366 A | 6/1995 | Reinhardt et al. |
| 5,433,204 A | 7/1995 | Olson |
| 5,433,207 A | 7/1995 | Pretlow, III |
| 5,438,554 A | 8/1995 | Seyed-Bolorforosh et al. |
| 5,443,071 A | 8/1995 | Banjanin et al. |
| 5,456,255 A | 10/1995 | Abe et al. |
| 5,456,257 A | 10/1995 | Johnson et al. |
| 5,469,849 A | 11/1995 | Sasaki et al. |
| 5,471,990 A | 12/1995 | Thirsk |
| 5,479,926 A | 1/1996 | Ustuner et al. |
| 5,482,046 A | 1/1996 | Deitrich |
| 5,523,058 A | 6/1996 | Umemura et al. |
| 5,526,816 A | 6/1996 | Arditi |
| 5,549,111 A | 8/1996 | Wright et al. |
| 5,551,433 A | 9/1996 | Wright et al. |
| 5,555,534 A | 9/1996 | Maslak et al. |
| 5,558,092 A | 9/1996 | Unger et al. |
| 5,560,364 A | 10/1996 | Porter |
| 5,570,691 A | 11/1996 | Wright et al. |
| 5,577,505 A | 11/1996 | Brock-Fisher et al. |
| 5,579,768 A | 12/1996 | Klesenski |
| 5,579,770 A | 12/1996 | Finger |
| 5,580,575 A | 12/1996 | Unger et al. |
| 5,581,517 A | 12/1996 | Gee et al. |
| 5,588,435 A | 12/1996 | Weng et al. |
| 5,598,845 A * | 2/1997 | Chandraratna et al. ..... 600/459 |
| 5,601,086 A | 2/1997 | Pretlow, III et al. |
| 5,608,690 A | 3/1997 | Hossack et al. |
| 5,617,862 A | 4/1997 | Cole et al. |
| 5,628,322 A | 5/1997 | Mine |
| 5,632,277 A | 5/1997 | Chapman et al. |
| 5,675,554 A | 10/1997 | Cole et al. |
| 5,678,554 A | 10/1997 | Hossack et al. |
| 5,685,308 A | 11/1997 | Wright et al. |
| 5,685,310 A | 11/1997 | Porter |
| 5,694,937 A | 12/1997 | Kamiyama |
| 5,696,737 A | 12/1997 | Hossack et al. |
| 5,709,210 A | 1/1998 | Green et al. |
| 5,724,976 A | 3/1998 | Mine et al. |
| 5,735,281 A | 4/1998 | Rafter |
| 5,833,613 A | 11/1998 | Averkiou et al. |
| 5,846,202 A * | 12/1998 | Ramamurthy et al. ...... 600/450 |
| 6,030,344 A * | 2/2000 | Guracar et al. ............. 600/447 |
| 6,086,539 A | 7/2000 | Guracar et al. |
| 6,102,858 A | 8/2000 | Hatfield et al. |
| 6,110,120 A | 8/2000 | Holley et al. |
| 6,126,603 A * | 10/2000 | Hatfield et al. ............. 600/454 |
| 6,174,287 B1 | 1/2001 | Resnick et al. |

OTHER PUBLICATIONS

"Supplement to Journal of the American College of Cardiology." American College of Cardiology, 45th Annual Scientific Session, Mar. 24–27, 1996 pp. 21A, 63A, 239–240A.

Abstracts Journal of the American Society of Echocardiography, vol. 8, No. 3 pp. 345–346, 355, 358–364.

B. Schrope, et al., "Simulated Capillary Blood Flow Measurement Using a Nonlinear Ultrasonic Contrast Agent." Ultrasonic Imaging 14 (1992).

Deborah J. Rubens, M.D., "Sonoelasticity Imaging of Prostate Cancer: In Vitro Results." Radiology, vol. 195, No. 2, 1995.

Excerpt from Ultrasonics: Fundamentals and Applications (1992), pp. 380–393, 363–365.

Fred Lee, Jr., M.D., "Sonoelasticity Imaging: Results in in Vitro TIssue Specimens." Radiology, vol. 181, No. 1 Oct. 1991.

H. Edward Karrer, et al., "A Phased Array Acoustic Imaging System for Medical Use." IEEE 1980 Ultrasonics Symposium.

J. Ophir, et al., "Elastography: A Quantitative Method for Imaging the Elasticity of Biological Tissues." Ultrasonic Imaging 13, (1991).

J.A. Hossack, et al., "Improving transducer performance using multiple active layers." SPIE vol. 1733 (1992).

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

K.J. Parker, et al., "Tissue Response to Mechanical Vibrations for 'Sonoelasticity Imaging'." Ultrasound in Med. and Biol., vol. 16, No. 3, (1990).

Ken Ishihara, et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Kevin J. Parker, PhD, et al., "Sonoelasticity of Organs: Shear Waves Ring a Bell." J. Ultrasound Med. 11 (1992).

Marc Gensane, "Bubble population measurements with a parametic array." J. Acoustical Society of America, 95 (6), Jun. 1994.

Michalakis A. Averkiou, et al. "Self–demodulation of amplitude and frequency. Modulated pulses in a thermouisceus fluid", J. Acoustical Society of America, vol. 94, No. 5, Nov. 1993.

Nico de Jong, "Physical properties and technical aspects of ultrasound contrast agents." (1 page).

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1995.

Robert M. Lerner, et al., "Sonoelasticity Images Derived from Ultrasound Signals in Mechanically Vibrated Tissues." Ultrasound in Med. and Biol., vol. 16, No. 3, 1990.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

V.L. Newhouse, et al., "Bubble size measurements using the nonlinear mixing of two frequencies." J. Acoustical Society of America, 75 (5), May 1984.

Vokmar Uhlendorf, et al., "Nonlinear Acoustical Response of Coated Microbubbles in Diagnostic Ultrasound." IEEE 1994 Ultrasonics Symposium.

William Armstrong et al., "Position Paper on Contrast Echocardiography", Am. Soc. of Echocardiography, Jun. 6, 1994.

Yang–Sub Lee, et al., "Time–domain modeling of pulsed finite–amplitude sound beams." J. Acoustical Society of America, 97 (2), Feb. 1995.

Kevin Wei, M.D. et al., Quantification of Myocardial Blood Flow With Ultrasound–Induced Destruction of Microbubbles Administered as a Constant Venous Infusion, American Heart Association, Inc., 1998.

* cited by examiner

TRANSMIT SPECTRUM
(TRIGGERED FRAMES)

TRANSMIT SPECTRUM
(LOCATOR FRAMES)

GATED ULTRASOUND IMAGING APPARATUS AND METHOD

This application is a division of application Ser. No. 09/378,236, filed Aug. 19, 1999, , which is a continuation of Ser. No. 08/838,919 now U.S. Pat. No. 6,112,120 (filed Apr. 11, 1997) and Ser. No. 09/159,527, now U.S. Pat. No. 5,957,845 filed Sep. 23, 1998.

BACKGROUND OF THE INVENTION

The present invention relates generally to ultrasound imaging systems, and more specifically to ultrasound imaging systems which provide improved visualization of contrast agents.

Ultrasound imaging systems usually are operated in a fashion to produce real-time moving images of a subject being scanned. These moving images are acquired as discrete static images, but at a high enough frame rate (typically 20–30 frames/sec) to present the illusion of a continuously moving image. Commercial ultrasound systems have also included triggered acquisition modes. In these modes, an ultrasound image frame is acquired at a specified point in each cardiac cycle, as measured for example by a delay from the R-wave of an ECG waveform. Typically the ultrasound system is quiescent between acquisition of successive triggered frames, neither transmitting nor receiving, and the system display is static, showing the last triggered frame. For example, an ultrasound system can be programmed to generate a triggered frame at 100 ms after each R-wave. At typical human heart rates of 60–120 beats/minute, this results in the image being updated at 1–2 frames/second, rather than the 20 or more frames/sec that might be possible if scanning were continuous. In other variants, triggered frames may be acquired only on selected beats (e.g., 150 ms after every 3rd R-wave), or multiple frames may be acquired per beat (e.g., 100, 150, and 250 ms after every 2nd R-wave).

One application where gated imaging modes are useful is imaging of ultrasound contrast agents. Contrast agents are injected into the bloodstream to increase the brightness of blood and blood-perfused tissues. However, these contrast agents (which are typically composed of stabilized gas microbubbles a few microns in diameter) are fragile and easily degraded (destroyed or altered) by the ultrasound pulses used to image them. A first ultrasound frame may show the contrast agent well, but subsequent frames often show less and less signal as the contrast agent is destroyed.

Thomas Porter and other researchers have demonstrated that gated imaging may be used to advantage where bubble destruction is an issue. A single image frame is acquired every cardiac cycle (or every few cardiac cycles). During the interval between frame acquisition, while the ultrasound transmitters are inactive, fresh contrast agent circulates into the tissues and vessels being imaged. Thus, if the interval between successive triggered frames is sufficiently long, a second acquired frame presents a signal that is as strong as the first. Some researchers have proposed that bubbles are not destroyed by ultrasound, but are altered in some way; during the interval between frames, the bubbles may recover in some way. In this case, the effect is the same: after an interval without transmission, the image returns to its initial brightness.

Another method used to reduce bubble destruction is to transmit at a reduced ultrasound intensity. This reduces bubble destruction at the cost of a reduced signal-to-noise ratio.

Another property of contrast agents that should be mentioned is non-linear scattering. Many contrast agents, when insonified with an acoustic pulse centered at one frequency, reflect or radiate ultrasound containing components at harmonics of the insonifying frequency as well as at the insonifying frequency. This property has been used to advantage in distinguishing contrast agents from normal tissues, which do not tend to scatter non-linearly. U.S. Pat. No. 5,255,683 (Monaghan), U.S. Pat. No. 5,410,516 (Uhlendorf), U.S. Pat. No. 5,456,257 (Johnson) and U.S. Pat. No. 5,577,505 (Brock-Fisher) disclose techniques for imaging non-linear scattering from tissues, and several ultrasound manufacturers are known to be developing second harmonic imaging capability (that is, forming an image from energy scattered at a harmonic multiple of twice the insonifying frequency). Harmonic imaging suffers from the same bubble destruction effects as does conventional fundamental imaging, and the same techniques of gating and reduced transmit power may be used.

Conventional gated imaging techniques require a user to hold an ultrasound probe in a fixed location for as long as several heartbeats without any visual feedback from the image, which statically show the previously acquired frame. Furthermore, static images of dynamic structures such as the heart may be difficult to interpret and may contain less diagnostic information than moving images. Reducing transmit power reduces bubble destruction, but makes the image noisier and ultimately limits the penetration depth (the maximum depth that may successfully be scanned). Transmit power reductions of 15 dB or more (below the maximum attainable by a typical diagnostic system under FDA limitations) may be required in order to avoid destroying bubbles when imaging perfusion of tissues. Transmit power reduction may be particularly disadvantageous in harmonic imaging. The harmonic component of the scattered and received signal is typically much smaller than the fundamental component (only a small fraction of the incident acoustic energy is converted to higher harmonic frequencies), while the noise floor remains roughly constant. Further, because of the non-linearity inherent in generating higher-order harmonics, a given reduction in transmit power results in an even greater reduction in the harmonic signal-strength. For example, a 3 dB transmit power reduction may result in roughly a 6 dB decrease in the level of the second harmonic signal.

SUMMARY OF THE INVENTION

The present invention is directed to an ultrasound imaging method and apparatus as defined by the following independent claims.

One preferred embodiment of the invention includes an ultrasound beamformer which acquires harmonic triggered frames using high transmit power responsive to a trigger signal derived from an ECG waveform. During the interval between acquisition of these triggered frames, additional image frames are acquired at reduced transmit power. In general, the in-between frames (referred to as "locator frames") are optimized for low levels of bubble degradation, possibly at the expense of image quality, while the triggered frames (also referred to as "imaging frames") are optimized primarily for image quality. Fundamental imaging is often preferred for the locator frames because it has a significantly higher signal-to-noise ratio than harmonic imaging, and hence can generate a usable image at much lower transmit power levels than would be required for useful harmonic imaging. These locator frames are displayed in real-time on a display device, providing the user with continuous feedback as to the location of the scan plane. The triggered frames may be displayed in real-time along with the locator frames in a variety of ways as described below, or may be reviewed later from memory with or without the locator frames.

In a broad sense, the invention includes any technique for alternating between two types of frames, one adapted to obtain a high-quality image of tissues containing contrast media and triggered intermittently, and a second adapted not to destroy the bubbles imaged by the first frame.

DETAILED DESCRIPTION OF THE PRESENTLY PREFERRED EMBODIMENTS

Figure 1:
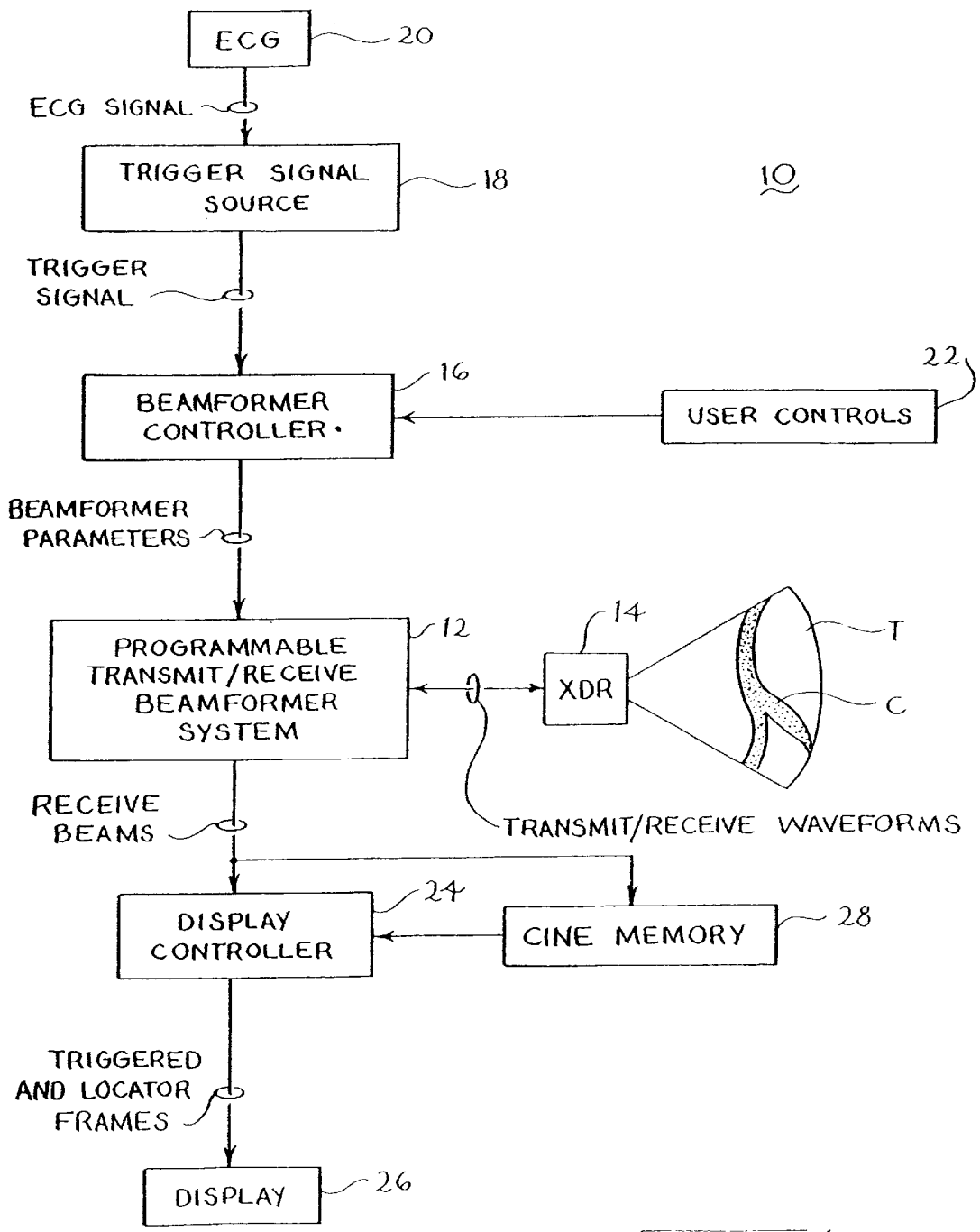
FIG. 1 is a schematic diagram of an ultrasound imaging system that incorporates preferred embodiments of the present invention.

Turning now to the drawings, FIG. 1 provides a schematic diagram of an ultrasound imaging system 10 that incorporates a presently preferred embodiment of this invention. The imaging system 10 includes a programmable transmit/receive beamformer system 12 that is coupled to an ultrasonic transducer 14. The beamformer system 12 provides transmit waveforms to the transducer 14 which cause the transducer 14 to emit ultrasonic energy into a tissue T containing a contrast agent C. Scattering sites within the tissue T, including the contrast agent C, return ultrasonic energy to the transducer 14, which transmits receive waveforms to the beamformer system 12. The region from which receive waveforms are collected will be referred to as the imaged region, and may include tissue, blood, and optionally contrast agent.

A beamformer controller 16 controls operation of the beamformer system 12 by controlling beamformer parameters such as transmit center frequency and bandwidth, receive center frequency and bandwidth, transmit power, receive gain, and transmit line spacing. The beamformer controller 16 is responsive to user controls 22 and to a trigger signal source 18. The trigger signal source 18 is responsive to an ECG signal supplied by an ECG device 20, and the trigger signal source 18 preferably includes conventional software or hardware which recognizes the R-wave of an ECG signal and generates a trigger signal when each R-wave occurs. The trigger signal is used as discussed below by the beamformer controller 16 to select appropriate beamformer parameters.

Detected, formed receive beams from the beamformer system 12 are sent to a display controller 24 which preferably includes a scan converter and generates triggered and locator frames as described below for immediate display on a display device 26. The beamformer system 12 is also coupled to a cine memory 28 which stores triggered and locator frames for later playback. The display controller 24 is capable of displaying superimposed locator frames and triggered frames on the same area of the screen of the display device 26 as they are acquired. Alternatively, locator frames may be displayed on different areas of the display screen from the triggered frames, as discussed below in conjunction with FIG. 6.

The present invention is directed to the structure and operation of the beamformer controller 16, and all of the remaining elements of FIG. 1 can be formed in any suitable manner, including a wide variety of conventional systems. The widest variety of trigger signal sources, beamformer controllers, beamformer systems, transducers, display controllers, displays, and cine memories can be adapted for use with this invention. Both analog and digital beamformer systems are suitable, and a wide variety of signals can be provided as inputs to the trigger signal source. By way of example, without intending any limitation, the ultrasound imaging system marketed by Acuson Corporation under the trade name Sequoia is capable of being modified to implement this invention.

Figure 2:
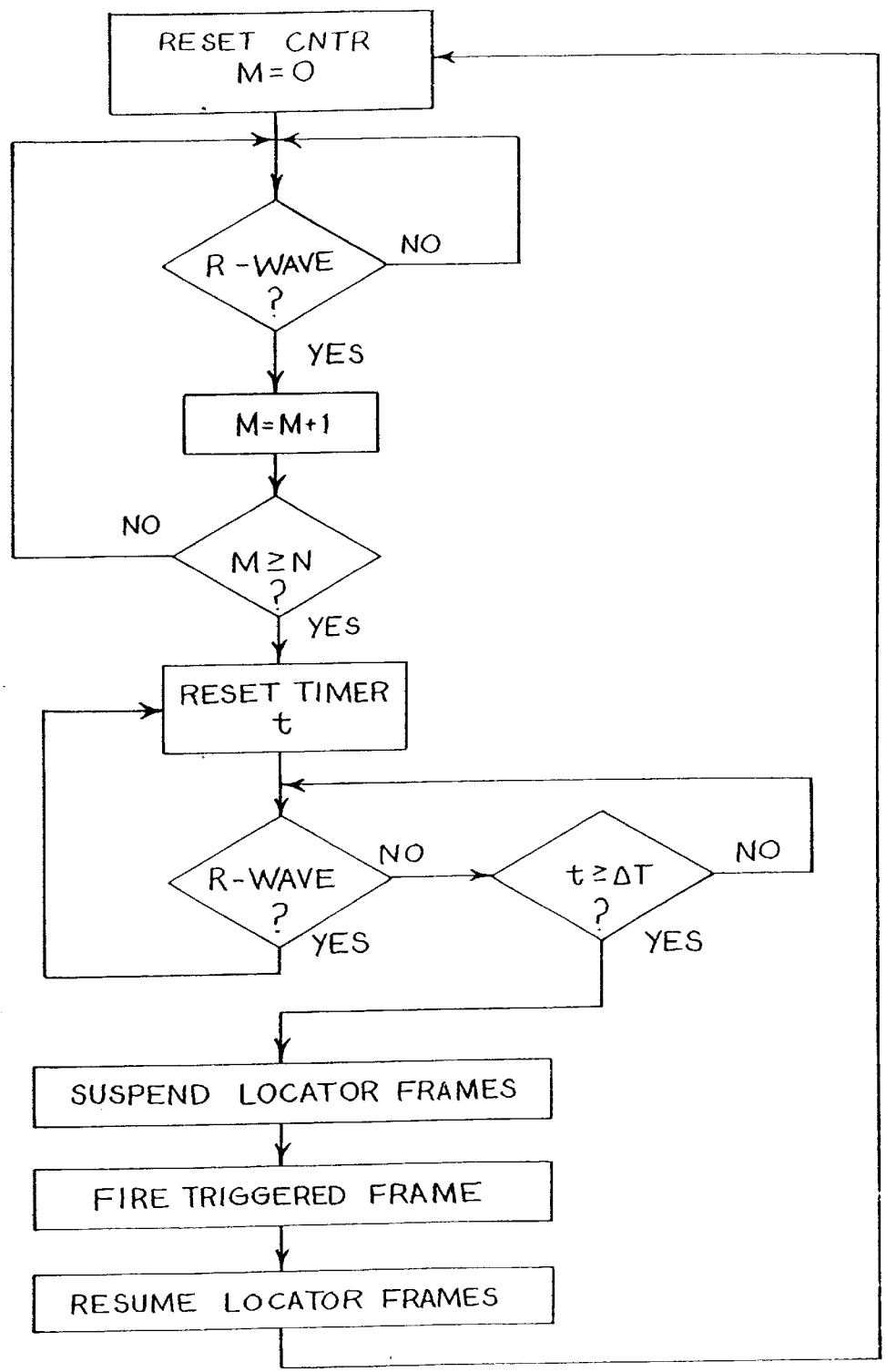
FIG. 2 is a flow chart illustrating operation of the beamformer controller of FIG. 1.

A flow chart illustrating one mode of operation of the beamformer controller 16 of FIG. 1 is given as FIG. 2. In this mode, the user selects a count of R-waves N and a programmable trigger delay $\Delta T$. A counter M is initially set to 0. The controller 16 counts R-waves until N R-waves have been detected, then initializes a timer t. When the programmed interval $\Delta T$ elapses without interruption by an R-wave, the controller suspends acquisition of any further locator frames after completion of any frame acquisition in progress. After locator frame acquisition has been completed, the controller changes beamformer parameters (setting the transmit power to maximum and selecting a harmonic receive center frequency), and acquires a single triggered frame. Following acquisition of the triggered frame, the controller changes beamformer parameters again (reducing the transmit power and selecting a fundamental receive center frequency) and resumes continuous firing of locator frames. The process then begins anew. The latter three steps of suspending locator frame acquisition, acquiring a triggered frame, and resuming locator frame acquisition are shown in more detail in FIG. 3.

As used herein, "harmonic" is intended broadly to include subharmonic and fractional harmonic energy (e.g. 1/2 or 3/2 of the fundamental frequency at which the transmit beam is centered) as well as higher harmonics (e.g. 2 or 3 times the fundamental frequency at which the transmit beam is centered). In addition, a harmonic image signal or frame may be acquired from a single frame of scan lines that are each fired once, or alternately a harmonic image signal or frame may be processed from multiple frames or from frames where individual scan lines are fired multiple times. See, for example, the harmonic images formed with subtractive processing in the above-identified Johnson and Brock-Fisher patents.

Figure 3:
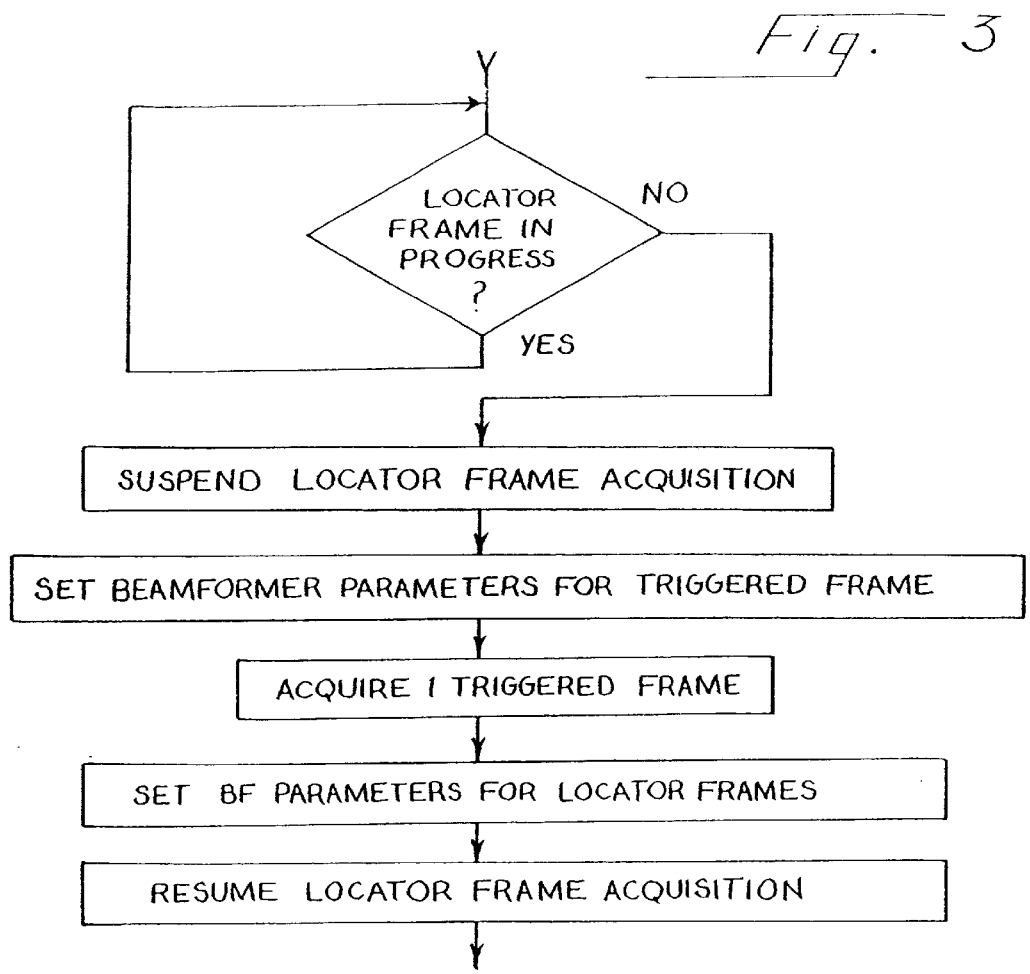
FIG. 3 is a flow chart providing further details regarding operation of the beamformer controller of FIG. 1.

Of course, various modifications to the flowcharts of FIGS. 2 and 3 present themselves, and these flowcharts should be taken as exemplary of one possible implementation of the invention. In particular, the flowchart of FIG. 2 shows one way of counting R-waves and measuring time delays; various other ways of counting and measuring are possible and can be substituted. The behavior of the system when the time comes to acquire a triggered frame can also be modified. Instead of waiting for an ongoing locator frame to be acquired, the controller can abort the locator frame in progress, discarding the partially acquired frame, so as to be able to begin the acquisition of the triggered frame as close to the desired time as possible, For cases where the trigger delay ΔT between R-wave and triggered frame is greater than the time required to acquire a locator frame, the controller may anticipate a coming triggered frame acquisition and suspend locator frame acquisition before the trigger delay ΔT has elapsed.

Figure 4:
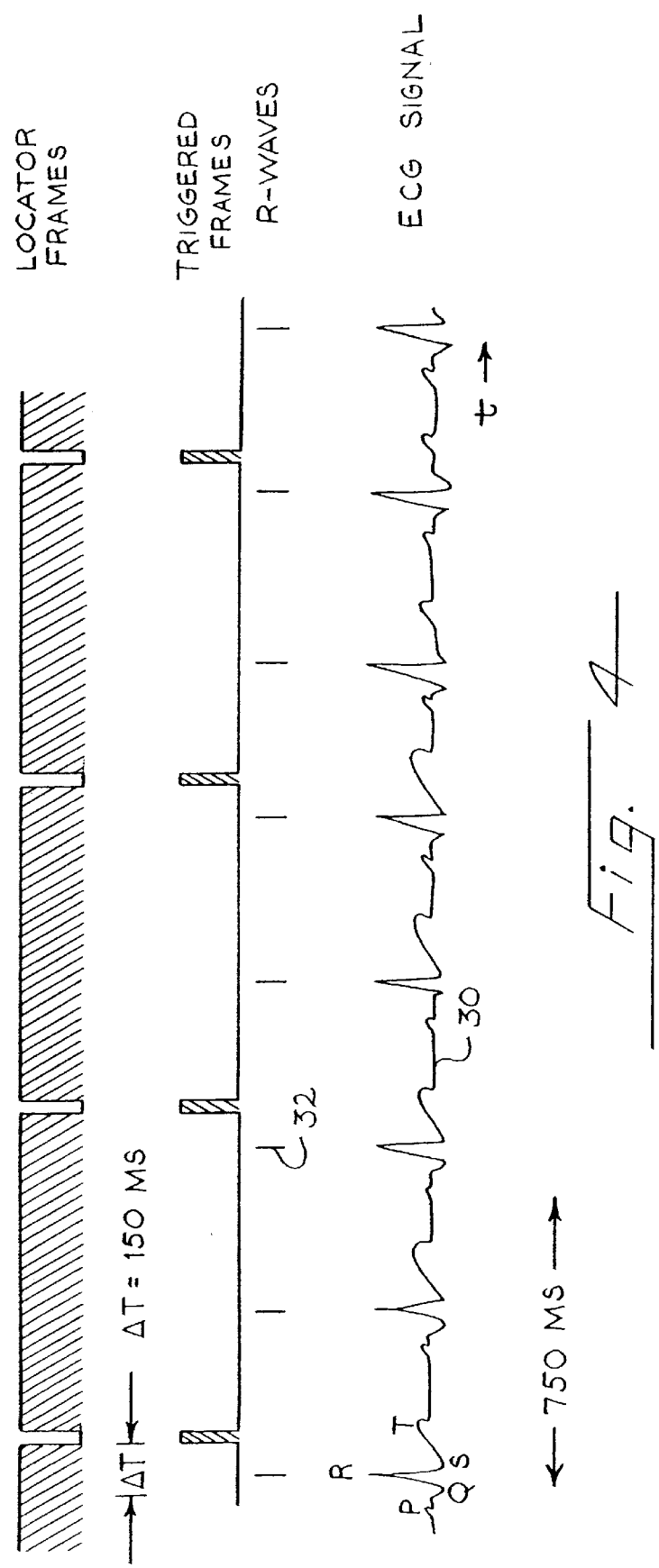
FIG. 4 is a timing diagram illustrating a first mode of operation of the imaging system of FIG. 1.

The operation of the system of FIG. 1 is illustrated schematically in FIG. 4. An ECG waveform 30 is shown across the bottom of the figure. Within the trigger signal source 18, conventional software or circuitry detects the peak of the R-wave, as illustrated by the vertical lines 32 above the ECG waveform 30. In this example, the interval between R-waves is 750 ms (heart rate=80 bpm) and the trigger signal source 18 generates a trigger signal 150 ms after every second R-wave (N=2, ΔT=150 ms). At each trigger, acquisition of locator frames is suspended, and a single triggered frame is acquired using alternate beamforming parameters such as those suggested above (harmonic imaging; high transmit power). Following acquisition of the triggered frame, acquisition of locator frames resumes using the appropriate beamformer parameters (fundamental imaging; low transmit power). In this implementation, both locator frames and imaging frames are directed to the screen as they are acquired, forming an apparently continuous image (with a flicker as each triggered frame is acquired). On later cine review, the triggered frames may be distinguished from the locator frames. Alternately, locator frames may be excluded from later cine review. Additionally the locator and image frames may be combined (optionally color-coding one image then adding the two together) into a single image. The user would then see a superposition of a relatively static image (the triggered frames) with a more dynamic one (the locator frames).

Figure 5A:
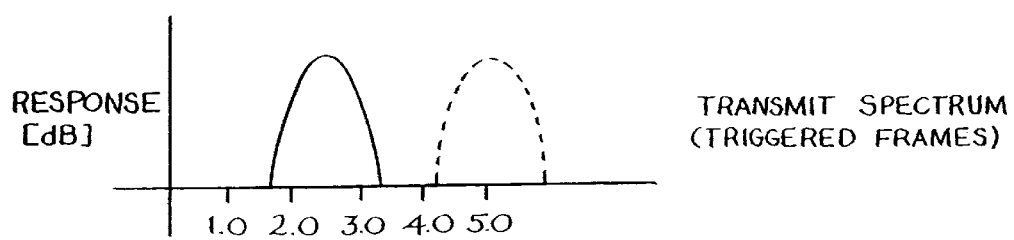
FIGS. 5a–5e are frequency diagrams of transmit and receive spectra for alternative modes of operation of the imaging system of FIG. 1.
Figure 5B:
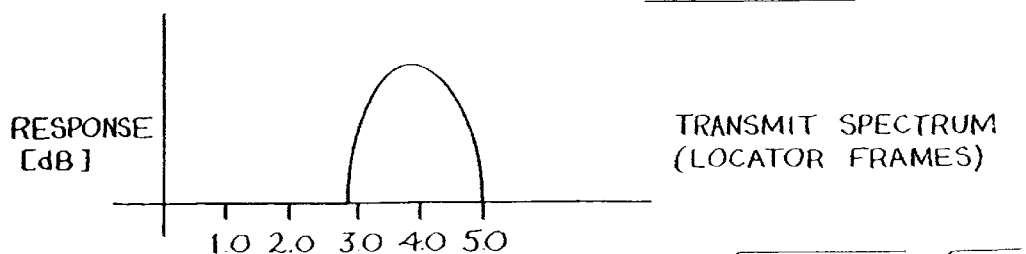

In addition to changing transmit power and selecting fundamental vs. harmonic imaging, the transmit center frequency, spectral shape, and/or bandwidth can be different for the locator and triggered frames. Contrast agents increase sound scattering through a resonance phenomenon, and the center frequency of that resonance varies inversely with bubble size. Bubbles of a given size scatter more energy (and may produce higher levels of harmonics) at or near the corresponding resonance frequency. At the same time, bubbles are more likely to be destroyed by ultrasound at or near their resonance frequency than by ultrasound away from their resonance frequency. Contrast agents achieve a broad bandwidth of contrast enhancement partly because each agent as injected includes many bubbles of different sizes and hence different resonance frequencies, FIGS. 5a–5d show how these properties of contrast agents may be used advantageously to reduce bubble destruction. FIG. 5a shows one preferred transmit spectrum for the triggered frames, centered at 2.5 MHz. The triggered frames may be acquired in fundamental or harmonic imaging (in which case the receive spectrum would be as shown by the dashed line curve); in either case, the greatest contribution to the image comes from bubbles with resonance near 2.5 MHz. FIG. 5b shows a preferred transmit spectrum of locator frames, centered (for example) at 4.0 MHz. While the locator frames may be optimized to minimize bubble destruction, some bubbles may be destroyed anyway. However, the destroyed bubbles will tend to have a resonance frequency at or near 4.0 MHz. Thus the bubbles destroyed by the locator frames are not those bubbles primarily imaged by the triggered frames. Additional benefit may be derived in this example from the fact that higher frequencies may tend to destroy bubbles to a lesser extent than lower frequencies.

Figure 5C:
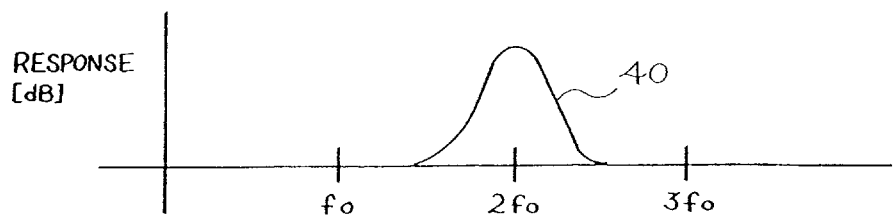
Figure 5D:
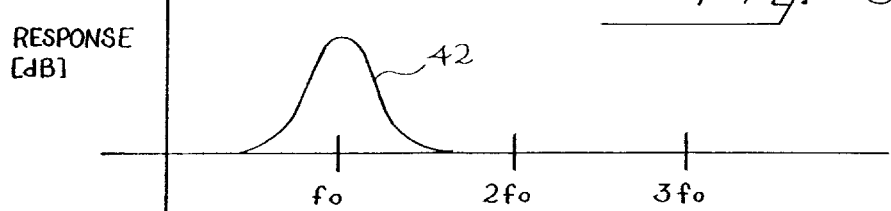
Figure 5E:
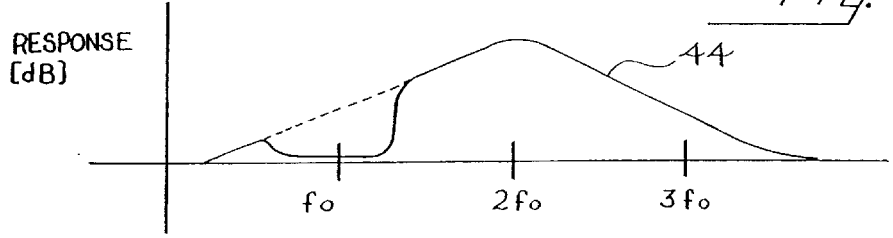

In general, the beamformer controller 16 of FIG. 1 may control the transmit waveform of the beamformer system 12 during locator frame acquisition to minimize or eliminate ultrasonic energy transmitted at and near the fundamental frequency $f_o$ of the triggered frames. Analog filters, pulse shapers, or digital filters may be used in the transmit beamformer to reduce ultrasonic energy transmitted at or near the fundamental frequency of the triggered frames. Preferably, the ultrasonic energy level at the fundamental frequency $f_o$ for each transmit pulse during locator frame acquisition is at least 6 dB, more preferably at least 12 dB or 20 dB, and most preferably at least 30 dB, below the ultrasonic energy level at the same frequency during triggered frame acquisition. In the preferred embodiment of FIG. 5c, the transmit waveforms are positioned in frequency to ensure that the spectrum 40 of the transmit waveforms for the locator frames has substantially no energy in a frequency band centered on the transmit frequency $f_o$ of the triggered frames. This band preferably extends on both sides of $f_o$ over a frequency range of one-tenth (more-preferably one-fifth) of $f_o$. Alternately, the band may extend on both sides of $f_o$ to frequencies at which the transmit waveforms for the triggered frames have an amplitude at least 6 dB below the amplitude at $f_o$. In this embodiment, the spectrum 42 of the transmit waveforms for the triggered frames has its peak energy level at $f_o$ (FIG. 5d). Of course, it is not critical that the spectrum 40 be centered at $2f_o$ as shown in FIG. 5c, and other center frequencies can readily be chosen. In the preferred embodiment of FIG. 5e, the spectrum 44 of the transmit waveform for the locator frames has been shaped or filtered in the region under the dotted line to substantially eliminate ultrasonic energy in a band centered on the transmit center frequency $f_o$ of the triggered frames.

Figure 6:
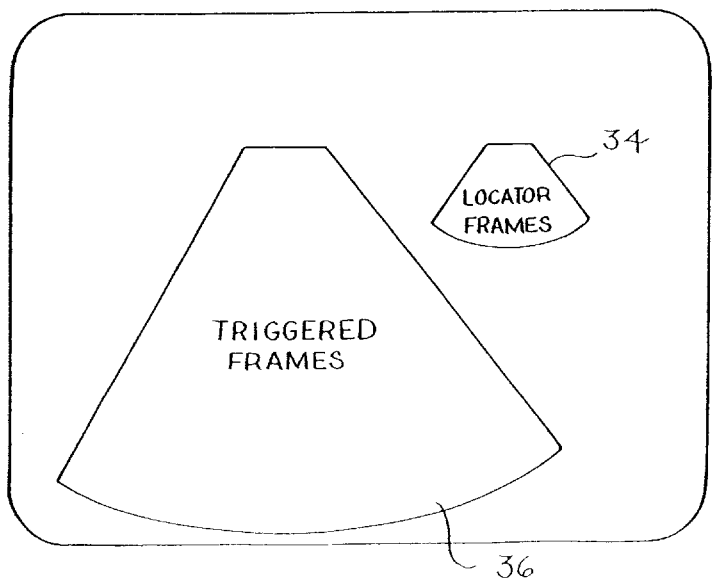
FIG. 6 is a schematic diagram of a display shown on the display device of FIG. 1.

Several different means of displaying the triggered and locator frames are possible. FIG. 6 shows one arrangement, in which the locator frames 34 are shown on a spatially separated region of the screen from the triggered frames 36. In the example, the locator frames 34 are shown as a small moving image situated apart from the relatively static (updated once every several cardiac cycles) triggered image 36.

Figure 7:
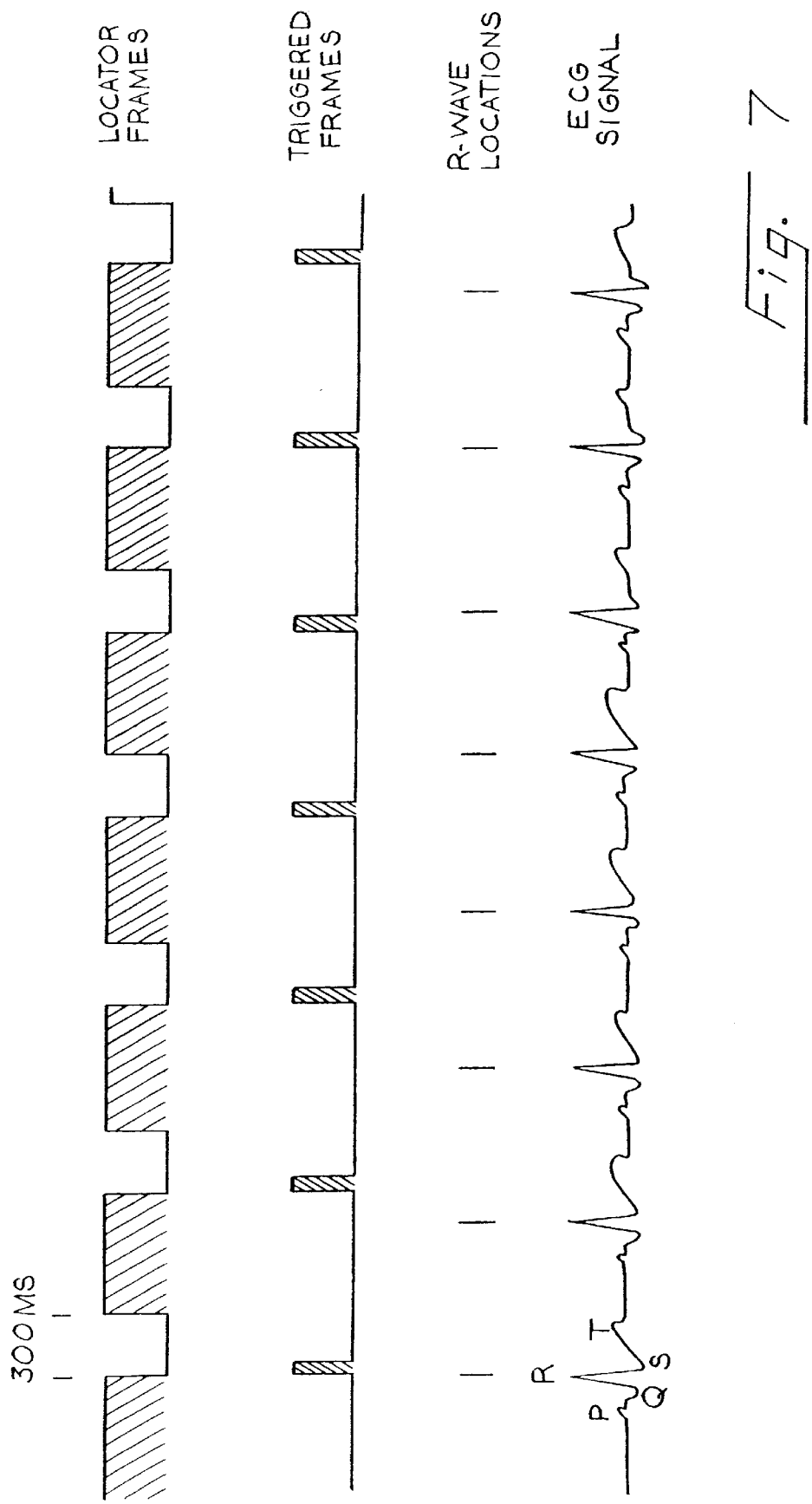
FIGS. 7 and 8 are timing diagrams for two additional modes of operation of the imaging system of FIG. 1.

An alternate mode of operation is illustrated in FIG. 7. In this case, locator frames are suspended when each triggered frame is fired, and for a selected period after acquisition of the triggered frame is completed. In FIG. 7, the total duration of suspension of the locator frames is 300 ms. The locator and triggered frames are displayed on the same area of the screen, so that the user sees a moving image (the locator frames) which periodically stops briefly (the triggered frames, each held for a persistence interval of 300 ms). In variations on this approach, the triggered or locator frames can be made more easily distinguishable from one another by changing their brightness or by color coding. In another variation, locator frames may be acquired during the hold period (once the triggered frame acquisition is complete), but not displayed. These frames are then available for later review. FIG. 7 also illustrates a multiple trigger mode of operation, which may be used independently of the persistence interval feature discussed above. The multiple trigger mode of operation is discussed below.

The embodiments described above improve upon the technique of using intermittent scanning to image fragile contrast agents by displaying a moving image even when the interval between triggered frame acquisition is large. This greatly eases the operator task of trying to hold the probe in a fixed position relative to the tissues being imaged in order to maintain a constant and appropriate scan plane. The locator frames are preferably formed using very low transmit power and so do not significantly destroy the contrast agent being imaged. While the triggered frames may destroy the contrast bubbles, the interval between triggered frames is large enough for the tissues being imaged to be refreshed with new contrast agent.

A further advantage of these embodiments is that a single ultrasound frame (the triggered frame) may be easier to interpret using the dynamic locator frames as context.

Many alternate methods of construction are possible. For example, the locator frames may be acquired at an artificially reduced frame rate. For example, if acquisition of a frame normally takes 25 ms (40 frames/sec), the locator frames can be acquired at 100 ms intervals (10 frames/sec) by adding dead time between adjacent scan lines or frames, further decreasing bubble destruction associated with acquisition of the locator frames. Even in this case, there are preferably more locator frames than triggered frames per unit time. Also, one or both of the triggered and locator frames may be acquired using a reduced line density. Reduced line density (with subsequent loss of resolution and loss of artifact) may be acceptable for the locator frames, and can be advantageous if used with an artificially reduced frame rate so that the frame rate is not increased as the line density is reduced. In this case, the reduced line density results in a reduced level of total ultrasound energy delivered into the subject being imaged, and hence in reduced bubble destruction. Reductions in line density may be beneficial for the triggered frames, as overly high line densities may result in excessive overlap of the transmit beams, resulting in bubble destruction (one ultrasound line firing destroying bubbles which would otherwise contribute to imaging of an adjacent line).

Another alternative is that triggered frames may be acquired using fundamental imaging instead of harmonic imaging. The locator frames should be optimized to reduce degradation of the bubbles imaged in the triggered frames. The locator frames may be acquired using different transmit center frequency, bandwidth, and/or pulse shape than the triggered frames. In general, any alteration in the transmit characteristics of the locator frames which results in less destruction of the bubbles preferably imaged in the triggered frames may be advantageous. In particular, using a different transmit center frequency may result in the triggering frames selectively destroying a population of bubbles different from those primarily contributing to the triggered frame images. In some embodiments, this observation may be exploited to fullest advantage by the use of hardware or software filtering means in the transmit beamformer to remove any components at the triggered frame transmit frequency from the locator frame transmit pulses. One or both of the locator frames and triggered frames can be acquired using a chirp, swept-spectrum, coded excitation, or other high time-bandwidth product transmit pulse. Such signals may attain a given signal-to-noise ratio with lower peak pressures than a conventional ultrasound pulse, and hence may provide better performance for a given level of bubble destruction. In some implementations, such techniques may degrade image quality by worsening axial response or by worsening focusing. Such tradeoffs may be acceptable for locator frames but not for triggered frames. In the event that such transmit signals are used, the receive beamformer should include means to restore the axial resolution as well as possible.

Figure 8:
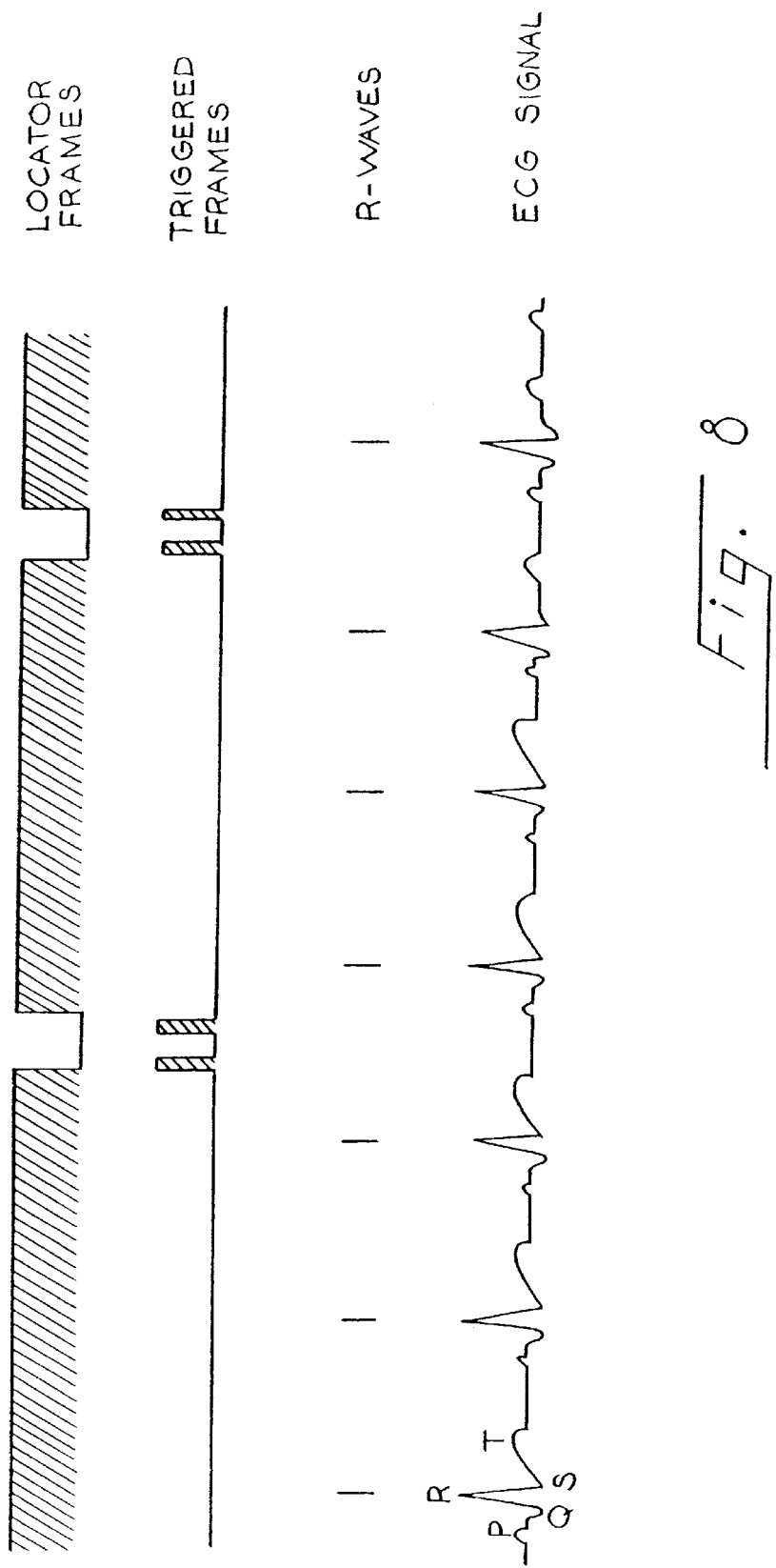

Instead of acquiring only a single triggered image frame, a selectable number of frames can be acquired in quick succession (continuous frame acquisition). Various complex trigger schemes can be used to determine when to acquire triggered frames. As a first example, multiple independently selectable trigger delays can be selected. An example is shown in FIG. 8, where two closely spaced triggered frames are acquired, 300 and 450 ms after every 3rd R-wave. In this example, the controller is programmed not to fire any locator frames during the time interval between the two triggered frames (which occur fairly close together). Trigger delays can be varied following each triggered frame to obtain sequences of triggered frames at various points in the cardiac cycle ("swept triggers"), as shown in FIG. 7. As an example, the first triggered frame is acquired immediately following the first R-wave. Subsequent triggered frames are acquired at 150, 300, 450, and 600 ms after the second through fifth R-waves, respectively. The cycle then repeats itself following the seventh R-wave. As a second example, triggered frames can be acquired at different time intervals after different R-waves; for example at 20 ms after every 1st, 4th, 7th, . . . R-wave; and at 500 ms after every 2nd, 5th, 8th . . . R-wave.

Various alternatives to ECG R-wave detection are possible: triggering can be based on a different feature of an ECG signal; an externally provided trigger signal; some other physiological measured signal such as respiration; or on a combination of signals (such as triggering on the first R-wave after the peak of a measured respiration signal, so as to compensate for breathing).

Figure 9:
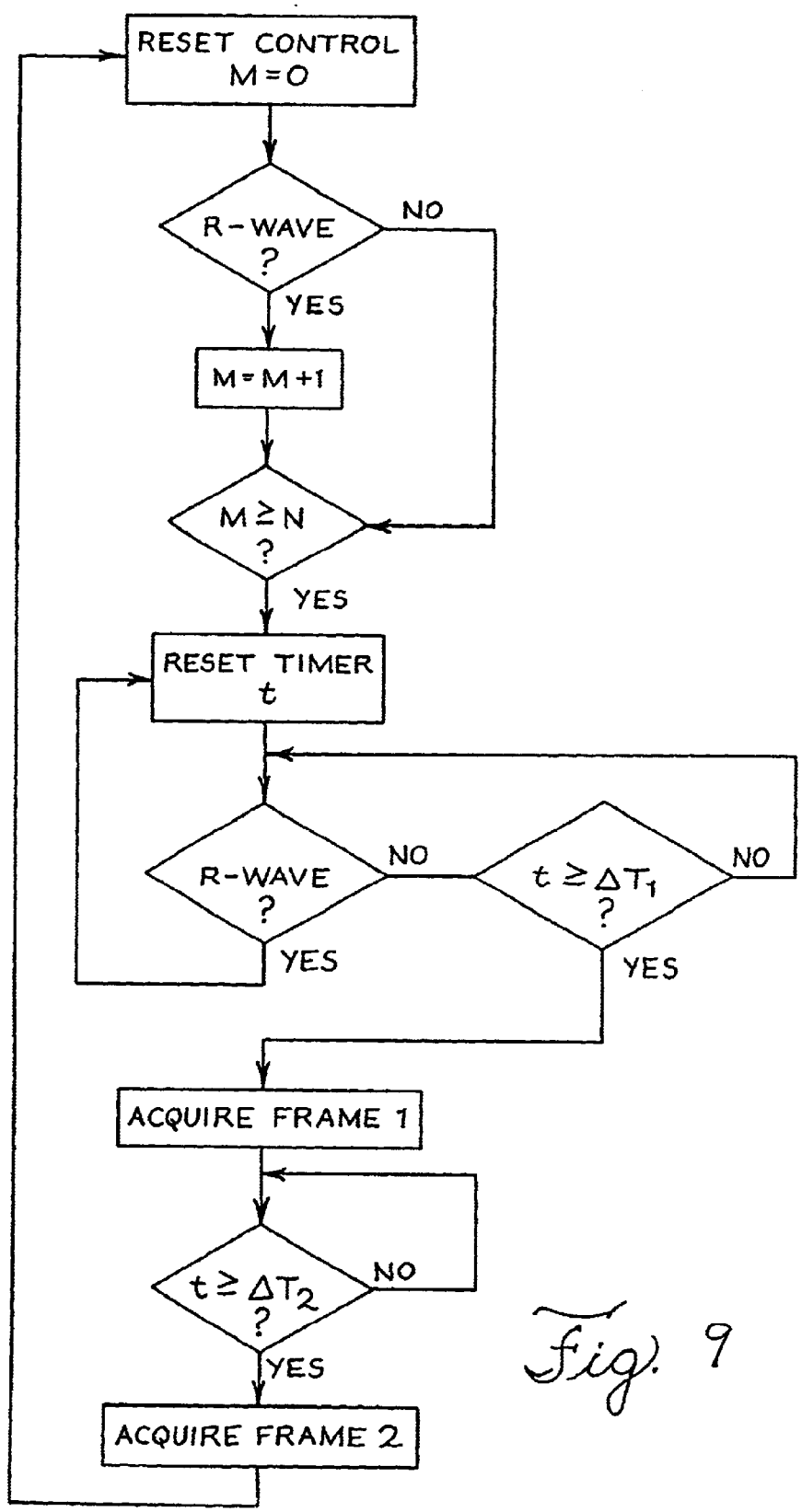
FIG. 9 is a flowchart showing a mode of operation of the controller 16 for acquiring sequences of triggered ultrasonic image frames.

Another aspect of the invention relates to the acquisition of multiple triggered frames, even in the absence of locator frames. For example, in the foregoing discussion two triggered frames are acquired after every third R-wave. FIG. 9 shows a flowchart for another mode of operation of the beamformer controller 16. In this mode, the user selects a count of R-waves N and two programmable trigger delays $\Delta T1$ and $\Delta T2$, with $\Delta T1$ less than $\Delta T2$. A counter M is initially set to zero. The con roller 16 counts R-waves until N R-waves have been detected, then initializes a timer T. When the first programmed interval $\Delta T1$ elapses without interruption by an R-wave, the controller acquires a first triggered frame. When the total interval $\Delta T2$ has elapsed since the timer was initialized (that is an additional time interval of $\Delta T2-\Delta T1$ after the first frame was acquired), the controller acquires a second triggered frame. The R-wave counter is then reset, and the entire process repeats. In this example, N is greater than 2.

This mode of operation may be generalized so that more than two frames are acquired, each specified by a respective time delay.

In an alternate mode of operation, after the first triggered frame is acquired, the counter may count a second number of R-waves N2, and a second time delay $\Delta T2$ before acquiring the second triggered frame. Again, this mode of operation may be generalized to more than two frames per sequence. For example, in the swept trigger sequence of FIG. 7, triggered frames are acquired with five different trigger delays after five respective R-waves. Following the fifth acquisition, the controller counts two R-waves before beginning the sequence anew.

In general, the R-wave can be considered as one example of a marker signal that occurs at a specified portion of an ECG wave. This aspect of the invention generates a marker signal such as an R-wave signal at a specified portion of a plurality of cycles of an ECG wave. Then a sequence of a plurality of triggered ultrasonic image frames is acquired, each frame timed to follow a respective marker signal by a respective time interval. In some cases two or more triggered ultrasonic image frames may share the same marker signal, in which case multiple ones of the triggered ultrasonic image frames will occur within a single cycle of the ECG wave. Following acquisition of this sequence of triggered ultrasonic image frames, acquisition of image frames is interrupted for at least one cycle of the ECG wave (two marker signals), before a next sequence of image frames is acquired.

As used herein, the term "responsive to" is intended broadly to cover any situation where a first element alters its operation in response to a signal generated by a second element, whether directly or indirectly. Thus, the first element is said to be responsive to the second when the first element responds directly to an output signal of the second element. Similarly, the first element is responsive to the second if intermediate elements or processors alter or modify a signal of the second element before it is applied as an input to the first element.

Many alternate methods of construction or use of the invention will be obvious to one skilled in the art, and the invention should not be limited to the specific examples or combinations discussed above. It is only the following claims, including all equivalents, which are intended to define the scope of this invention.

We claim:

1. In an ultrasound imaging system comprising: a programmable transmit/receive beamformer system operative to generate transmit waveforms and responsive to ultrasonic signals radiated by a region of a body, the improvement comprising:

a trigger signal source; and a beamformer controller coupled with the trigger signal source and the beamformer system, said controller operative to cause the beamformer system to acquire multiple triggered frames at different intervals, a first of the triggered frames acquired after a first count of signal periods from the trigger signal source and a second of the triggered frames acquired after a second count of signal periods from the trigger signal source, the second count being started after the first count.

2. The system of claim 1 wherein the trigger signal source is responsive to an ECG signal.

3. The system of claim 2 wherein the signal periods comprise heart cycles and the first and second counts differ by an integral number of heart cycles.

4. The system of claim 1 wherein the different intervals are programmed.

5. The system of claim 4 further comprising a user interface for programming the different intervals by selection of the first and second counts.

6. The system of claim 1 wherein the beamformer controller automatically programs said beamformer system for intermittent first periods of triggered transmission of pulses and intermittent second periods of locator frame operation between at least some of the first periods, said transmission pulses for the first periods differing from the transmission pulses for the second periods in at least one of the following parameters: transmit power, transmit center frequency, transmit line spacing, receive center frequency, transmit bandwidth, transmit spectral shape.

7. The system of claim 6 wherein transmit power is greater in the first periods than the second periods.

8. The system of claim 6 wherein transmit line spacing is closer in the first periods than the second periods.

9. The system of claim 1 wherein the transmit beamformer system is operable to acquire triggered frames to enhance image quality and is operable to acquire locator frames between the triggered frames to reduce contrast agent degradation.

* * * * *